(12) United States Patent
Nariyuki et al.

(10) Patent No.: US 9,465,116 B2
(45) Date of Patent: Oct. 11, 2016

(54) RADIOGRAPHIC IMAGE DETECTION DEVICE

(71) Applicant: FUJIFILM Corporation, Tokyo (JP)

(72) Inventors: Fumito Nariyuki, Ashigarakami-gun (JP); Toshiyuki Nabeta, Ashigarakami-gun (JP); Yoshihiro Okada, Ahigarakami-gun (JP); Hirotaka Watano, Ashigarakami-gun (JP); Munetaka Kato, Ashigarakami-gun (JP); Haruyasu Nakatsugawa, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 14/670,070

(22) Filed: Mar. 26, 2015

(65) Prior Publication Data

US 2015/0204986 A1    Jul. 23, 2015

Related U.S. Application Data

(63) Continuation of application No. PCT/JP2013/072661, filed on Aug. 26, 2013.

(30) Foreign Application Priority Data

Sep. 27, 2012    (JP) ................... 2012-213877

(51) Int. Cl.
*G01T 1/20* (2006.01)
*G01T 1/202* (2006.01)
(Continued)

(52) U.S. Cl.
CPC .......... *G01T 1/2018* (2013.01); *A61B 6/4233* (2013.01); *A61B 6/4283* (2013.01); *G01T 1/161* (2013.01); *G01T 1/202* (2013.01)

(58) Field of Classification Search
CPC ... G01T 1/2018; G01T 1/161; G01T 1/1612; G01T 1/164; G01T 1/1642; G01T 1/20; G01T 1/208; G01T 1/362
See application file for complete search history.

(56) References Cited

U.S. PATENT DOCUMENTS

2003/0062481 A1* 4/2003 Okada ................... G01T 1/2018
                                              250/361 R
2007/0257198 A1* 11/2007 Ogawa .................. G01T 1/2002
                                              250/370.11

(Continued)

FOREIGN PATENT DOCUMENTS

JP    2001-330677 A    11/2001
JP    2006-52980 A     2/2006

(Continued)

OTHER PUBLICATIONS

Machine Translation JP 2012-137441.*

(Continued)

*Primary Examiner* — Yara B Green
(74) *Attorney, Agent, or Firm* — Birch, Stewart, Kolasch & Birch, LLP

(57) ABSTRACT

A monocoque-structured housing accommodates a photoelectric conversion panel, a scintillator, and a circuit board in this order from an X-ray incidence side. The scintillator contains cesium iodide and converts X-rays into visible light. The scintillator is vapor-deposited on the photoelectric conversion panel. A plurality of pixels that photoelectrically convert the visible light into charges are formed in the photoelectric conversion panel. A signal processor, which reads out the charge from each pixel and generates image data, is mounted on the circuit board. A gap layer is formed between the scintillator and the circuit board.

11 Claims, 11 Drawing Sheets

(51) Int. Cl.
 *A61B 6/00* (2006.01)
 *G01T 1/161* (2006.01)

(56) References Cited

U.S. PATENT DOCUMENTS

| | | | |
|---|---|---|---|
| 2007/0272873 A1* | 11/2007 | Jadrich | G01T 1/20 250/370.11 |
| 2012/0126124 A1 | 5/2012 | Nakatsugawa et al. | |
| 2012/0153170 A1 | 6/2012 | Nariyuki | |
| 2012/0168632 A1* | 7/2012 | Yagi | A61B 6/4233 250/366 |
| 2012/0181438 A1* | 7/2012 | Watanabe | G01T 1/2018 250/366 |
| 2013/0001425 A1* | 1/2013 | Nakatsugawa | G01T 1/2018 250/366 |
| 2014/0042331 A1* | 2/2014 | Konkle | G01T 1/2018 250/369 |

FOREIGN PATENT DOCUMENTS

| | | | |
|---|---|---|---|
| JP | 2010-237138 A | | 10/2010 |
| JP | 2012-105879 A | | 6/2012 |
| JP | 2012-133315 A | | 7/2012 |
| JP | 2012-137441 | * | 7/2012 |
| JP | 2012-141291 A | | 7/2012 |

OTHER PUBLICATIONS

International Search Report issued in PCT/JP2013/072661, Oct. 29, 2013.
PCT/ISA/237—Issued in PCT/JP2013/072661, Oct. 29, 2013.
Chinese Office Action and Search Report dated Oct. 27, 2015, for Chinese Application No. 201380050808.4 with the English translation of the Office Action.
Chinese Office Action, dated Jun. 1, 2016, for Chinese Application No. 201380050808.4, along with an English translation.

* cited by examiner

RADIOGRAPHIC IMAGE DETECTION DEVICE

CROSS-REFERENCE TO RELATED APPLICATIONS

This application is a Continuation of PCT International Application No. PCT/JP2013/072661 filed on Aug. 26, 2013, which claims priority under 35 U.S.C. §119(a) to Japanese Patent Application No. 2012-213877, filed Sep. 27, 2012. Each of the above application(s) is hereby expressly incorporated by reference, in its entirety, into the present application.

BACKGROUND OF THE INVENTION

1. Field of the invention

The present invention relates to a radiographic image detection device used for radiographic imaging.

2. Description Related to the Prior Art

Recently, radiographic image detection devices have been used for diagnostic imaging in medical fields. The radiographic image detection device converts radiation (for example, X-rays) applied from a radiation source and passed through an object of interest of a subject (patient) into charges and produces a radiographic image. There are direct-conversion type and indirect-conversion type radiographic image detection devices. The direct-conversion type radiographic image detection device directly converts the radiation into the charges. The indirect-conversion type radiographic image detection device converts the radiation into visible light, and then converts the visible light into the charges.

The indirect-conversion type radiographic image detection device comprises a scintillator (phosphor layer) and a photoelectric conversion panel. The scintillator absorbs the radiation and converts the absorbed radiation into the visible light. The photoelectric conversion panel detects the visible light and converts the detected visible light into the charges. The scintillator is made from cesium iodide (CsI) or gadolinium oxide sulfur (GOS). The photoelectric conversion panel is composed of an insulating substrate made from glass, and thin-film transistors and photodiodes arranged in a matrix over the surface of the insulating substrate.

Manufacturing cost using the CsI is more expensive than that using the GOS. However the CsI is superior in efficiency of converting the radiation into the visible light. The CsI has a columnar crystal structure and due to its light-guide effect, the CsI is superior in SN ratio of image data. For these reasons, the CsI is particularly used for the scintillators of high-end radiographic image detection devices.

"Laminated type" and "direct vapor deposition type" radiographic image detection devices, which utilize the CsI as the scintillator, are known. In the laminated type radiographic image detection device, a vapor deposition base, on which the scintillator is vapor-deposited, and the photoelectric conversion panel are laminated or adhered to each other through an adhesive layer such that the scintillator faces the photoelectric conversion panel. In the laminated type radiographic image detection device, distal end portions (hereinafter simply referred to as the end portions) of the columnar crystals of the CsI are in close proximity to the photoelectric conversion panel. The visible light released from the end portions enters the photoelectric conversion panel efficiently, so that a radiographic image with high resolution is produced. However, the use of the vapor deposition base in the laminated type radiographic image detection device increases manufacturing processes, resulting in high manufacturing cost.

In the direct vapor deposition type, the scintillator is directly vapor-deposited on the photoelectric conversion panel. The vapor deposition base is unnecessary in the direct vapor deposition type, so that the direct vapor deposition type has few manufacturing processes and low manufacturing cost. Since the end portions of the columnar crystals of the CsI of the direct vapor deposition type are disposed on the opposite side of the photoelectric conversion panel, the image quality of the radiographic image is inferior to that of the laminated type, but superior to that of the case where the scintillator is made from the GOS. Thus the direct vapor deposition type offers an excellent balance between performance and cost.

However, the direct vapor deposition type has a drawback that a part of the columnar crystals may grow abnormally or irregularly during the vapor deposition of the scintillator on the photoelectric conversion panel. Distal end portions (or simply referred to as the end portions) of the abnormally-grown columnar crystals (hereinafter referred to as the abnormally-grown crystals) may significantly protrude from the surface of the scintillator (see Japanese Patent Laid-Open Publication No. 2006-052980). The abnormally-grown crystals are columnar crystals grown on a local defect or the like having a convex shape or the like occurred on the photoelectric conversion panel. The size of the end portions of the abnormally-grown crystals expands to be greater than the size of the defect, on which the abnormally-grown crystals grow, as the end portions become away from the photoelectric conversion panel.

In the radiographic image detection device described in the Japanese Patent Laid-Open Publication No. 2006-052980, the scintillator is disposed on the radiation source side. In other words, the scintillator is disposed closer to the radiation source than is the photoelectric conversion panel. The radiation enters the scintillator from the end portions of the columnar crystals. The scintillator absorbs the radiation at around the end portions and generates the visible light. The configuration in which the scintillator is disposed closer to the radiation source than is the photoelectric conversion panel is referred to as PSS (Penetration Side Sampling) type.

In the PSS type, the radiation is incident on the end portions of the columnar crystals. In the case where the abnormally-grown crystals are present, the end portions of the abnormally-grown crystals also generate the light. Since the end portions of the abnormally-grown crystals expand significantly, the end portions generate a high amount of light, which causes an image defect in a radiographic image. To prevent or reduce the image defect, the end portions of the abnormally-grown crystals are crushed by application of pressure or the like after the scintillator is vapor-deposited on the photoelectric conversion panel.

ISS (Irradiation Side Sampling) type radiographic image detection devices of the direct vapor deposition type are known. In the ISS type, which has the configuration contrary to that of the PSS type, the photoelectric conversion panel is disposed closer to the radiation source than is the scintillator (see, for example, U.S. Patent Application Publication No. US 2012/0126124 A1 (corresponding to Japanese Patent Laid-Open Publication No. 2012-105879) and Japanese Patent Laid-Open Publication No. 2001-330677). In the ISS type, the radiation from the radiation source passes through the photoelectric conversion panel and then enters the scintillator. The scintillator generates the light in its portions on the radiation incidence side, close to the photoelectric conversion panel. Thereby, the light-receiving efficiency of the photoelectric conversion panel is improved. Thus, the ISS type produces radiographic images excellent in image quality and brightness.

In the ISS-type radiographic image detection device of the direct vapor deposition type, the radiation is incident on the photoelectric conversion panel side of the scintillator. Even if the abnormally-grown crystals are present, the radiation is incident on the proximal end portions of the abnormally-grown crystals and hardly reaches the distal end portions of the abnormally-grown crystals. For this reason, the amount of light generated in the distal end portions is small. In the ISS-type, the abnormally-grown crystals have little influence on the image, so that it is unnecessary to crush the end portions of the abnormally-grown crystals.

In a case where the photoelectric conversion panel with the scintillator is accommodated in a housing without crushing the end portions of the abnormally-grown crystals, the end portions, which protrude from the surface of the scintillator, may come into contact with the housing or the like and break when a load is imposed on the housing. The breakage of the end portions of the abnormally-grown crystals may cause damage to the adjacent normal columnar crystals. Since a circuit board, on which a signal processor for generating image data and the like are mounted, faces the scintillator in the ISS type, the end portions of the abnormally-grown crystals are likely to come into contact with and be crushed by the circuit board.

SUMMARY OF THE INVENTION

An object of the present invention is to provide an ISS type radiographic image detection device which prevents damage to a scintillator.

In order to achieve the above and other objects, the radiographic image detection device of the present invention comprises a scintillator, a photoelectric conversion panel, a circuit board, a gap layer, and a housing. The scintillator contains cesium iodide and converts radiation into visible light. The scintillator is vapor-deposited on the photoelectric conversion panel. A plurality of pixels, which photoelectrically converts the visible light into charges, are formed in the photoelectric conversion panel. The circuit board is provided with a signal processor. The signal processor generates image data based on the charges generated by the photoelectric conversion panel. The gap layer is provided between the scintillator and the circuit board. The gap layer is provided with a first support. One of ends of the first support is fixed to the circuit board and the other end of the first support supports the scintillator. The housing accommodates the photoelectric conversion panel, the scintillator, the gap layer, and the circuit board in this order from a radiation incidence side on which the radiation is incident from a radiation source at the time of imaging.

It is preferred that the scintillator has a non-columnar crystal layer and a plurality of columnar crystals formed on the non-columnar crystal layer. The non-columnar crystal layer is in close contact with the photoelectric conversion panel.

It is preferred that the first support supports a peripheral portion of the scintillator. It is preferred that the first support is an elastic body.

It is preferred that the radiographic image detection device further comprises a second support for supporting between the photoelectric conversion panel and the circuit board. It is preferred that the second support surrounds the scintillator.

It is preferred that the housing has a monocoque structure. It is preferred that the photoelectric conversion panel and the circuit board are individually fixed to the housing.

It is preferred that the radiographic image detection device further comprises a sealing film that surrounds the scintillator. It is preferred that the radiographic image detection device further comprises a light-reflecting film that reflects the visible light released from end portions of the columnar crystals.

It is preferred that the radiographic image detection device further comprises a protective film that covers the end portions of the columnar crystals. In this case, it is preferred that the light-reflecting film is formed over the protective film and the sealing film covers the light-reflecting film.

It is preferred that the pixel has a photodiode, which converts the visible light into the charge, and a switching element, which reads out the charge generated by the photodiode.

It is preferred that the radiographic image detection device further comprises a light-permeable base, which transmits the visible light, on the opposite side of the radiation incidence side of the photoelectric conversion panel. In this case, the scintillator is vapor-deposited on the light-permeable base. It is preferred that the light-permeable base is an OPS film.

According to the radiographic image detection device of the present invention, the gap layer is provided between the scintillator and the circuit board. Owing to this, the radiographic image detection device prevents damage to the scintillator.

BRIEF DESCRIPTION OF THE DRAWINGS

The above and other objects and advantages of the present invention will be more apparent from the following detailed description of the preferred embodiments when read in connection with the accompanied drawings, wherein like reference numerals designate like or corresponding parts throughout the several views, and wherein.

DESCRIPTION OF THE PREFERRED EMBODIMENTS

Figure 1:
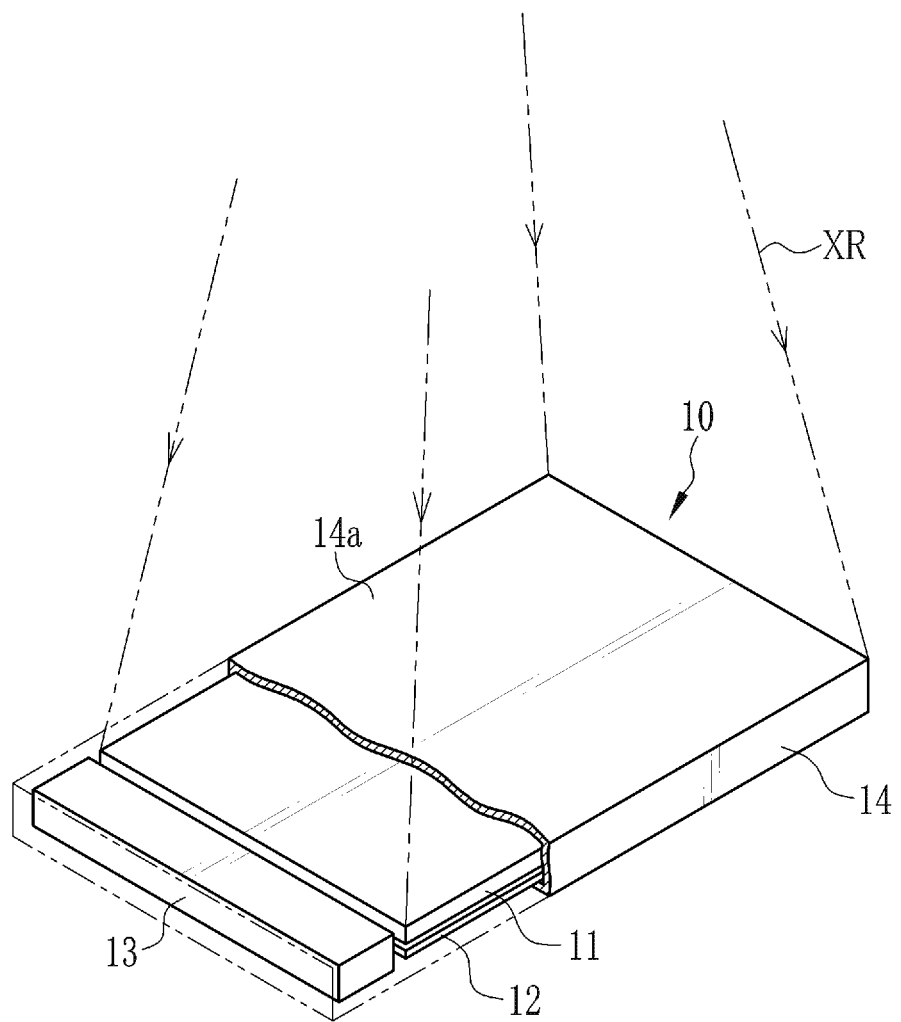
FIG. 1 is a partially-exploded perspective view of an X-ray image detection device.

In FIG. 1, an X-ray image detection device 10 comprises a flat panel detector (FPD) 11, a circuit board 12, a control unit 13, and a housing 14. The housing 14 accommodates the FPD 11, the circuit board 12, and the control unit 13. The housing 14 has an integral monocoque structure made from lightweight carbon fiber reinforced plastics (or carbon fiber) having high X-ray (XR) transmission property and high durability.

One of the sides of the housing 14 is formed with an opening (not shown). The FPD 11, the circuit board 12, and the control unit 13 are inserted into the housing 14 through the opening at the time of manufacture of the X-ray image detection device 10. A lid (not shown) is attached so as to cover the opening after the insertion.

At the time of imaging, X-rays XR emitted from an X-ray source 60 (see FIG. 5) and passed through a subject (patient) 61 (see FIG. 5) are applied to a top surface (hereinafter referred to as the exposure surface) 14a of the housing 14. The exposure surface 14a is provided with alignment mark(s) (not shown) to align the X-ray source 60 and the subject 61.

The size of the X-ray image detection device 10 is the same or substantially the same as that of a conventional X-ray film cassette. The X-ray image detection device 10 is used in place of the conventional X-ray film cassette, and referred to as "electronic cassette".

The FPD 11 and the circuit board 12 are disposed in the housing 14 in this order from the exposure surface 14a side, to which the X-rays XR are applied at the time of imaging. The circuit board 12, on which integrated circuit (IC) chips for signal processing and the like are mounted, is fixed to the housing 14. The control unit 13 is disposed near one of the shorter sides of the housing 14.

The control unit 13 incorporates a microcomputer and a battery (both not shown). To control the operation of the FPD 11, the microcomputer communicates with a console (not shown), which is connected to the X-ray source 60, through a wired or wireless communicator (not shown).

Figure 2:
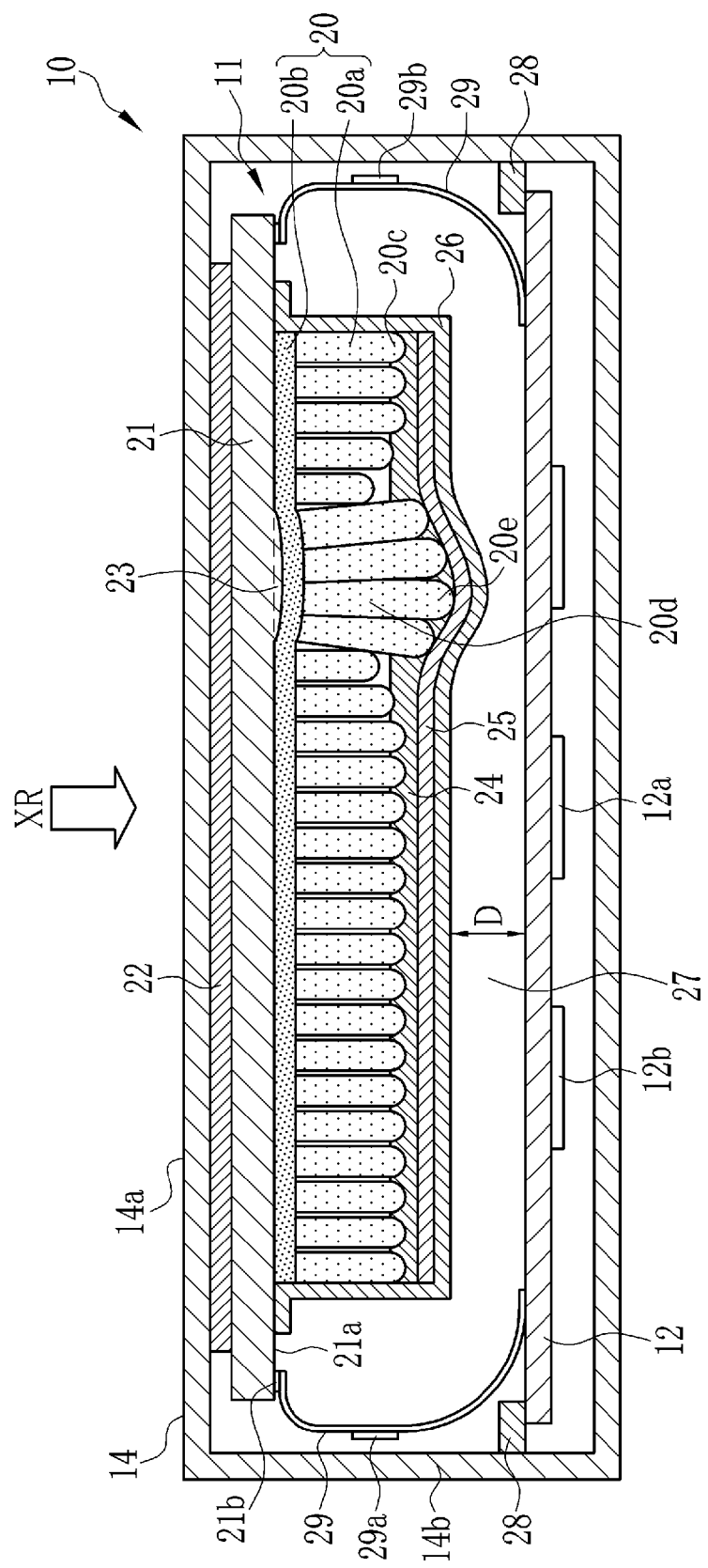
FIG. 2 is a cross-sectional view of the X-ray image detection device.

In FIG. 2, the FPD 11 comprises a scintillator 20 and a photoelectric conversion panel 21. The scintillator 20 converts the X-rays XR into visible light. The photoelectric conversion panel 21 converts the visible light into charges. The X-ray image detection device 10 is of ISS (Irradiation Side Sampling) type. The photoelectric conversion panel 21 and the scintillator 20 are disposed in this order from the X-ray (XR) incidence side (the exposure surface 14a side) on which the X-rays XR are incident at the time of imaging. The scintillator 20 absorbs the X-rays XR which have passed through the photoelectric conversion panel 21, and generates the visible light. The photoelectric conversion panel 21 receives the visible light released from the scintillator 20, and photoelectrically converts the visible light into the charges.

The X-ray incidence side of the photoelectric conversion panel 21 is adhered or affixed to the inner face, on the exposure surface 14a side, of the housing 14 through an adhesive layer 22. The adhesive layer 22 is made from polyimide or the like.

The scintillator 20 is formed by vapor deposition of thallium-activated cesium iodide (CsI:Tl) on a surface 21a of the photoelectric conversion panel 21. The scintillator 20 has a plurality of columnar crystals 20a and a non-columnar crystal layer 20b. The non-columnar crystal layer 20b is formed on the photoelectric conversion panel 21 side. The columnar crystals 20a grow on the non-columnar crystal layer 20b. The columnar crystals 20a have their distal end portions (hereinafter simply referred to as the end portions) 20c on the opposite side of the non-columnar crystal layer 20b.

The plurality of columnar crystals 20a are formed on the non-columnar crystal layer 20b. Each columnar crystal 20a is spaced from its adjacent columnar crystal by a gap. The refractive index of the columnar crystal 20a is approximately 1.81, which is greater than the refractive index (approximately 1.0) of the gap (air), so that the columnar crystal 20a has light-guide effect. Due to the light-guide effect, most of the visible light generated in each columnar crystal 20a is transmitted therethrough and enters the photoelectric conversion panel 21 through the non-columnar crystal layer 20b.

In a case where there is a defect 23, which is a partially deformed portion with a convex shape or the like, is present on the surface 21a of the photoelectric conversion panel 21, the CsI:Tl deposited on the defect 23 grows abnormally or irregularly during the vapor deposition, and becomes an abnormally-grown crystal 20d that is greater in diameter and length than the normal columnar crystal 20a. A distal end portion (hereinafter simply referred to as the end portion) 20e of the abnormally-grown crystal 20d protrudes, in the direction opposite the photoelectric conversion panel 21, from the surface of the scintillator 20.

A protective film 24 is formed to cover the end portions 20c of the columnar crystals 20a and the end portions 20e of the abnormally-grown crystals 20d. The protective film 24 is made from hot-melt resin. The hot-melt resin is adhesive resin composed of 100% nonvolatile thermoplastic material. The hot-melt resin is solid at room temperature and does not contain water or solvent. The protective film 24 contains light-reflecting fine particles (not shown). The light-reflecting fine particles are metal fine particles (e.g. gold, silver, aluminum, nickel, or the like) or metal oxide (e.g. titanium dioxide ($TiO_2$), silicon dioxide ($SiO_2$), aluminum oxide ($Al_2O_3$) or the like). The protective film 24 is formed by, for example, melting hot-melt resin in which the light-reflecting fine particles are dispersed, and applying the hot-melt resin with the light-reflecting fine particles onto the surface of the scintillator 20, with the use of a coating device.

A light-reflecting film 25, which is made from metal (e.g. aluminum (Al) or the like) is formed on the surface of the protective film 24. The light-reflecting film 25 is, for example, laminated or stacked over the protective film 24. The protective film 24 and the light-reflecting film 25 reflect the visible light, which is emitted or released from the end portions 20c of the columnar crystals 20a, back into the columnar crystals 20a, thereby improving efficiency for converting the X-rays XR into charges.

A sealing film 26 is formed to cover the light-reflecting film 25 and the sides of the scintillator 20. The sealing film 26 is formed by a thermal CVD (Chemical Vapor Deposition) method. The scintillator 20 is sealed between the sealing film 26 and the photoelectric conversion panel 21. The sealing film 26 is formed from poly-para-xylylene (or poly-para-xylene) that is resistant to moisture, for example, Parylene C (registered trademark, a product of Japan Parylene Co.).

The circuit board 12 is disposed on the opposite side of the X-ray incidence side of the scintillator 20 through a gap layer (gap) 27 having the width (distance) D. The gap layer 27 is filled with air. The circuit board 12 is fixed to fixing members 28 with screws, adhesive, or the like. The fixing members 28 are fixed to respective sides 14b of the housing 14. The distance D is a distance between the circuit board 12 and the sealing film 26 of the scintillator 20.

The distance D is determined to allow for the estimated maximum length of the abnormally-grown crystal 20d so as to prevent the circuit board 12 from coming into contact with the sealing film 26 and pressing the scintillator 20 (particularly, the end portions 20e of the abnormally-grown crystals 20d). The distance D is determined to allow for a usage temperature range to prevent the sealing film 26 from coming in contact with the circuit board 12 even if the scintillator 20 is warped (or curved) due to a change in temperature.

The circuit board 12 and the photoelectric conversion panel 21 are electrically connected to each other through a flexible printed circuit board 29. The flexible printed circuit board 29 is connected to an external terminal 21b, which is provided at an end of the photoelectric conversion panel 21, by a so-called TAB (Tape Automated Bonding) method.

A gate driver 29a and a charge amplifier 29b are mounted as IC chips on the flexible printed circuit board 29. The gate driver 29a drives the photoelectric conversion panel 21. The charge amplifier 29b converts the charge, which is outputted from the photoelectric conversion panel 21, into a voltage signal. A signal processor 12a and an image memory 12b are mounted as IC chips on the circuit board 12. The signal processor 12a generates image data based on the voltage signals converted by the charge amplifier 29b. The image memory 12b stores the image data.

Figure 3:
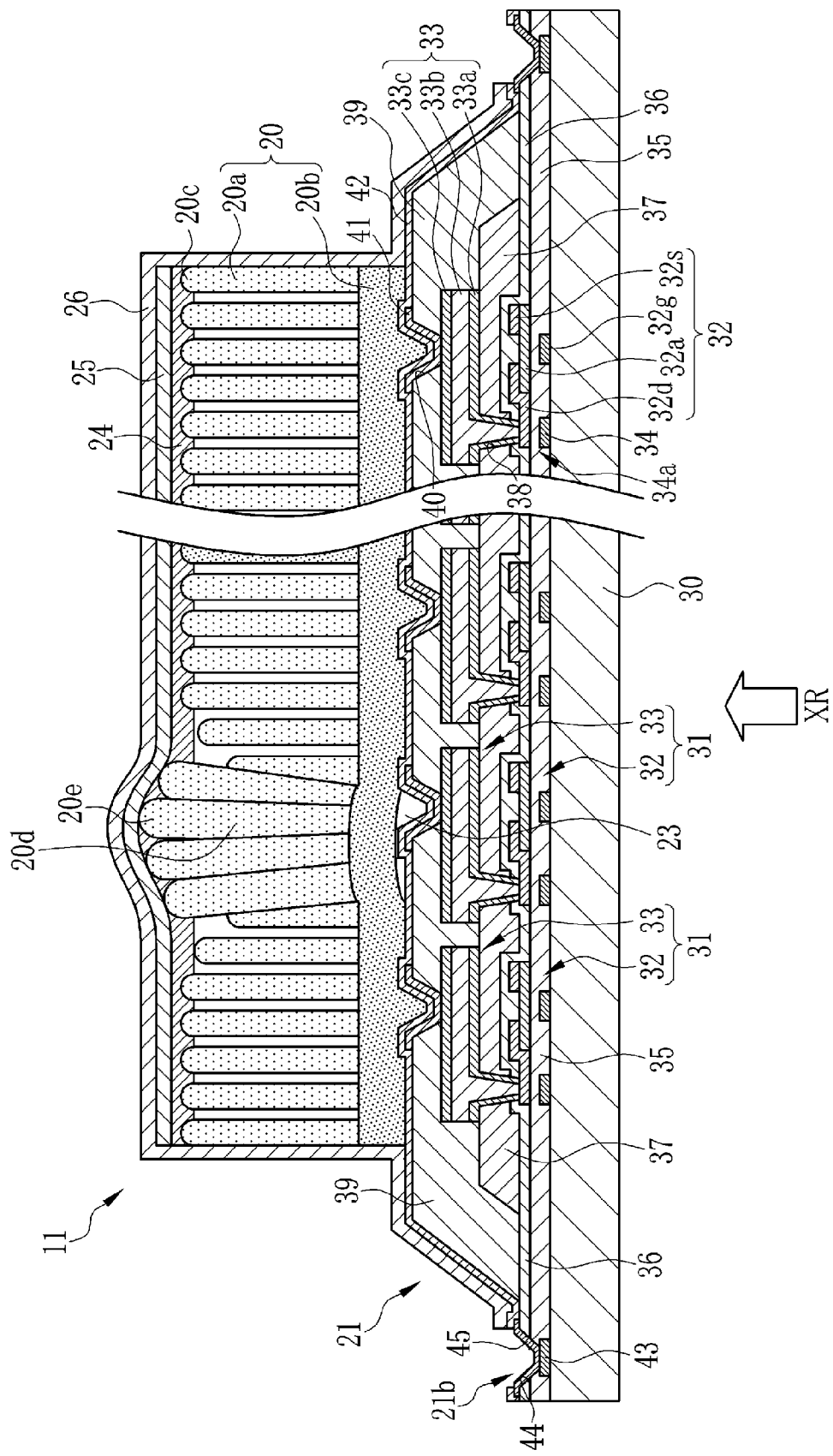
FIG. 3 is a cross-sectional view of an FPD.

In FIG. 3, the photoelectric conversion panel 21 comprises an insulating substrate 30 made from glass (e.g. non-alkali glass or the like) and a plurality of pixels 31 arranged over the insulating substrate 30. It is preferred that the thickness of the insulating substrate 30 is less than or equal to 0.5 mm to improve X-ray (XR) transmission property.

Each pixel 31 has a thin film transistor (TFT) 32 and a photodiode (PD) 33 connected to the TFT 32. The PD 33 photoelectrically converts the visible light, which is generated by the scintillator 20, into a charge and stores the charge. The TFT 32 is a switching element, which reads out the charge stored in the PD 33.

The TFT 32 comprises a gate electrode 32g, a source electrode 32s, a drain electrode 32d, and an active layer 32a. The TFT 32 is of an inverted staggered type, in which the gate electrode 32g is disposed in a layer located below the layer of the source electrode 32s and the drain electrode 32d. The gate electrode 32g is formed over the insulating substrate 30. To increase a charge storage capacity of each pixel 31, a charge storage electrode 34 is formed over the insulating substrate 30. A ground voltage is applied to the charge storage electrode 34.

An insulating film 35, which is made from silicon nitride (SiNx) or the like, is formed over the insulating substrate 30 so as to cover the gate electrode 32g and the charge storage electrode 34. The active layer 32a is formed over the insulating film 35 so as to face the gate electrode 32g. The source electrode 32s and the drain electrode 32d are disposed apart from each other by a predetermined distance over the active layer 32a. A part of the drain electrode 32d extends over the insulating film 35. The drain electrode 32d is opposed to the charge storage electrode through the insulating film 35, thereby constituting a capacitor 34a.

The gate electrode 32g, the source electrode 32s, the drain electrode 32d, and the charge storage electrode 34 are formed from aluminum (Al) or cupper (Cu). The active layer 32a is formed from amorphous silicon. A TFT protecting film 36, which is made from silicon nitride ($SiN_x$) or the like, is formed over the insulating film 35 so as to cover the source electrode 32s, the drain electrode 32d, and the active layer 32a.

A first planarizing film 37 is formed over the TFT protecting film 36 so as to planarize the uneven surface caused by the TFT 32. The first planarizing film 37 is formed by applying (or coating) organic material. The surface of the first planarizing film 37 is planarized or flat. A contact hole 38, which is in a position opposing the drain electrode 32d, is formed through the first planarizing film 37 and the TFT protecting film 36. The PD 33 is connected to the drain electrode 32d of the TFT 32 through the contact hole 38. The PD 33 is composed of a lower electrode 33a, a semiconductor layer 33b, and an upper electrode 33c.

The lower electrode 33a is formed over the first planarizing film 37 so as to cover the inside of the contact hole 38 and also to cover the TFT 32. The lower electrode 33a is connected to the drain electrode 32d. The lower electrode 33a is formed from aluminum (Al) or indium tin oxide (ITO). The semiconductor layer 33b is stacked or layered over the lower electrode 33a. The semiconductor layer 33b is made from PIN-type amorphous silicon, and comprises $n^+$ layer, i layer, and $p^+$ layer stacked or layered in this order from the bottom. The upper electrode 33c is formed over the semiconductor layer 33b. The upper electrode 33c is formed from material with high light-transmitting property such as indium tin oxide (ITO) or indium zinc oxide (IZO).

A second planarizing film 39 is formed over the PD 33 and the first planarizing film 37 so as to planarize the uneven surface caused by the PD 33. Similar to the first planarizing film 37, the second planarizing film 39 is formed by applying or coating organic material, and has a planarized or flat surface.

A contact hole 40 is formed through the second planarizing film 39 to expose the upper electrode 33c. A common electrode line 41 is connected to the upper electrode 33c through the contact hole 40. The common electrode line 41 is connected to and shared by the upper electrode 33c of each of the PDs 33, and applies a bias voltage to the upper electrodes 33c. The upper electrode 33c is formed from aluminum (Al) or cupper (Cu).

An insulating protective film 42 is formed over the second planarizing film 39 and the common electrode line 41. The insulating protective film 42 is formed from silicon nitride ($SiN_x$) or the like, as in the case of the TFT protecting film 36.

The external terminal 21b is provided over the insulating substrate 30 and outside of the second planarizing film 39. The external terminal 21b is composed of a terminal electrode 43 and a metal film 45. The terminal electrode 43 is formed over the insulating substrate 30. The metal film 45 covers a contact hole 44 formed through the insulating film 35 and the TFT protecting film 36.

The scintillator 20 is formed over the flat surface of the second planarizing film 39 through the insulating protective film 42. To be more specific, the non-columnar crystal layer 20b is formed over the insulating protective film 42 through vacuum vapor deposition. The non-columnar crystal layer 20b is composed of a plurality of particulate crystals with small distances between them. In other words, the non-columnar crystal layer 20b has a high space-filling ratio. For this reason, the non-columnar crystal layer 20b is highly adhesive to the insulating protective film 42. The columnar crystals 20a grow on the non-columnar crystal layer 20b through the vacuum vapor deposition. The diameter of the columnar crystal 20a is in the order of 6 μm, and substantially constant in the lengthwise direction of the columnar crystal 20a.

The thickness of the scintillator 20 is preferred to be greater than or equal to 400 μm to improve X-ray (XR) absorption efficiency.

As described above, in the case where the defect 23 is present on the surface of the photoelectric conversion panel 21, the abnormally-grown crystals 20d grow over the defect 23.

As described above, the protective film 24 is formed to cover the end portion 20c of each columnar crystal 20a and the end portion 20e of each abnormally-grown crystal 20d. The light-reflecting film 25 is formed over the surface of the protective film 24. The sealing film 26 is formed to surround the scintillator 20.

Figure 4:
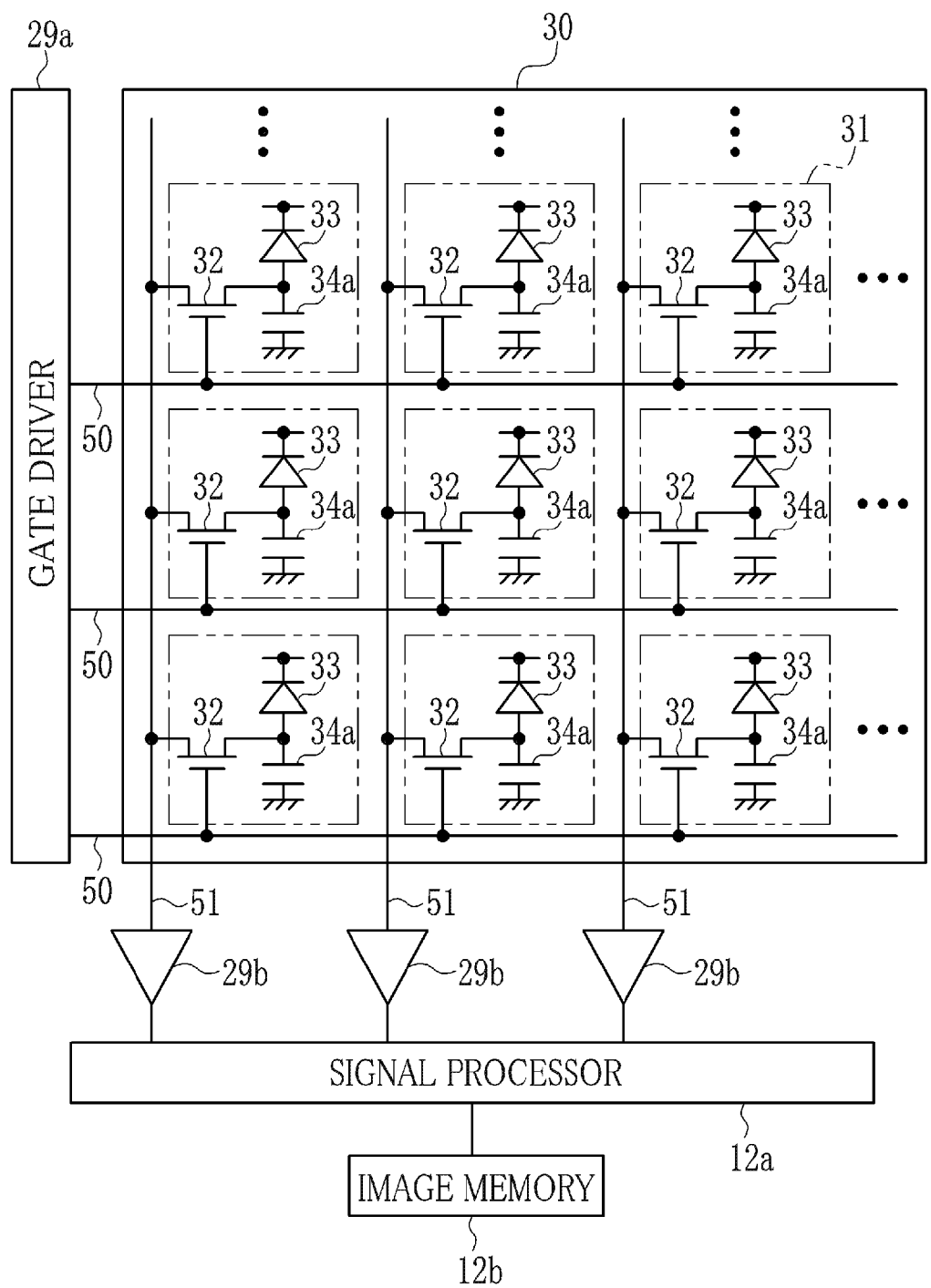
FIG. 4 is a circuit diagram of a photoelectric conversion panel.

In FIG. 4, the pixels 31 are arranged in a two-dimensional matrix over the insulating substrate 30. As described above, each pixel 31 comprises the TFT 32, the PD 33, and the capacitor 34a. Each pixel 31 is connected to a gate line 50 and a data line 51. Each gate line 50 extends in a row direction. The plurality of gate lines 50 are arranged in a column direction. Each data line 51 extends in the column direction. The plurality of data lines 51 are arranged in the row direction to cross the gate lines 50. The gate line 50 is connected to the gate electrode 32g of the TFT 32. The data line 51 is connected to the drain electrode 32d of the TFT 32.

An end of the gate line 50 is connected to the gate driver 29a. An end of the data line 51 is connected to the charge amplifier 29b. The gate driver 29a provides the gate drive signals to the respective gate lines 50 sequentially, to turn on the TFTs 32 connected to each gate line 50. In response to turning on the TFT 32, the charges stored in the PD 33 and the capacitor 34a are outputted to the data line 51.

The charge amplifier 29b has a capacitor (not shown) for storing the charge. The charge amplifier 29b integrates the charge outputted to the data line 51, and converts the charge into a voltage signal. The signal processor 12a performs A/D conversion, gain correction processing, and the like on the voltage signal outputted from the charge amplifier 29b, to generate image data. The image memory 12b is composed of a flash memory or the like, and stores the image data generated by the signal processor 12a. The image data stored in the image memory 12b is readable externally through a wired or wireless communicator (not shown).

Figure 5:
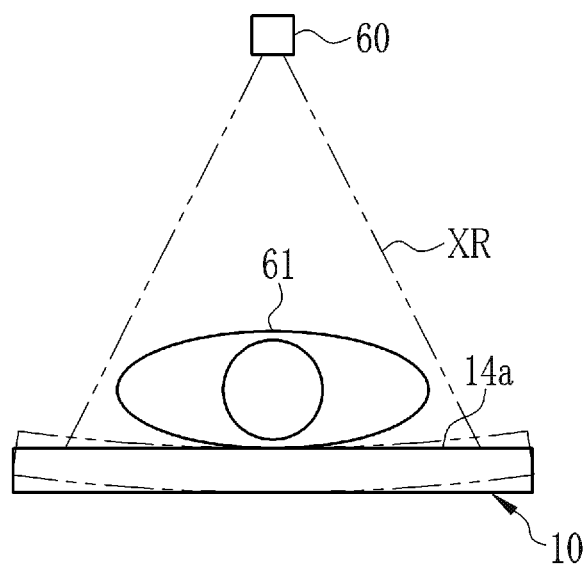
FIG. 5 is an explanatory view illustrating the X-ray image detection device in use.

Next, an operation of the X-ray image detection device 10 is described. To perform imaging using the X-ray image detection device 10, an operator (e.g. radiologic technologist) places the subject 61 on the X-ray image detection device 10 and places the X-ray source 60 so as to face the subject 61 as illustrated in FIG. 5.

The console is operated to command the start of imaging. In response to this, the X-ray source 60 emits the X-rays XR. The X-rays XR passed through the subject 61 are applied to the exposure surface 14a of the X-ray image detection device 10. The X-rays XR applied to the exposure surface 14a pass through the adhesive layer 22 and the photoelectric conversion panel 21 in this order, and then enters the scintillator 20.

The scintillator 20 absorbs the X-rays XR and generates the visible light. The visible light is generated mostly in portions, inside the columnar crystals 20a, on the non-columnar crystal layer 20b side. The visible light generated in the columnar crystals 20a is transmitted through the respective columnar crystals 20a due to the light-guide effect, and then passes through the non-columnar crystal layer 20b. Thereafter, the visible light enters the photoelectric conversion panel 21. The protective film 24 and the light-reflecting film 25 reflect the visible light, transmitted inside the columnar crystals 20a to the end portions 20c and emitted from the end portions 20c, back into the columnar crystals 20a. The reflected visible light passes through the non-columnar crystal layer 20b and then enters the photoelectric conversion panel 21.

The PD 33 of each pixel 31 converts the visible light, which has entered the photoelectric conversion panel 21, into a charge. The charge is stored in the PD 33 and the capacitor 34a. In response to the completion of the X-ray emission from the X-ray source 60, the gate driver 29a applies the gate drive signals sequentially to the gate electrodes 32g of the TFTs 32 through the gate lines 50. Thereby the TFTs 32, arranged in the row direction, are turned on sequentially in the column direction. The charges stored in the PDs 33 and the capacitors 34a are outputted to the data line 51 through the turned-on TFTs 32.

The charge amplifier 29b converts the charge, which has been outputted to the data line 51, into a voltage signal and inputs the voltage signal to the signal processor 12a. The signal processor 12a generates the image data based on the voltage signals of all the pixels 31. The image data is stored in the image memory 12b.

During the imaging, the X-ray image detection device 10 may bend slightly due to the weight of the subject 61 as illustrated by two-dot chain lines in FIG. 5. The housing 14 has a monocoque structure, so that it's lightweight but likely to bend because of its low load-carrying capacity. The X-ray image detection device 10 is of the ISS type, in which the photoelectric conversion panel 21 is disposed on the exposure surface 14a side. The weight of the subject 61 exerts on the photoelectric conversion panel 21 through the housing 14.

The scintillator 20 bends as the photoelectric conversion panel 21 bends. However, the gap layer 27 with the specific width (distance) D is provided between the scintillator 20 and the circuit board 12 facing (or opposed to) the scintillator 20. The gap layer 27 prevents the scintillator 20 from coming into contact with the circuit board 12 and being damaged. Since the distance D is determined to allow for the length of the abnormally-grown crystal 20d, the gap layer 27 also prevents the end portion 20e of the abnormally-grown crystal 20d from being pressed and damaged by the circuit board 12. Thus, the X-ray image detection device 10 according to this embodiment produces an X-ray image with little image detect because the gap layer 27 prevents the damage to the end portion 20e of the abnormally-grown crystal 20d.

Figure 6:
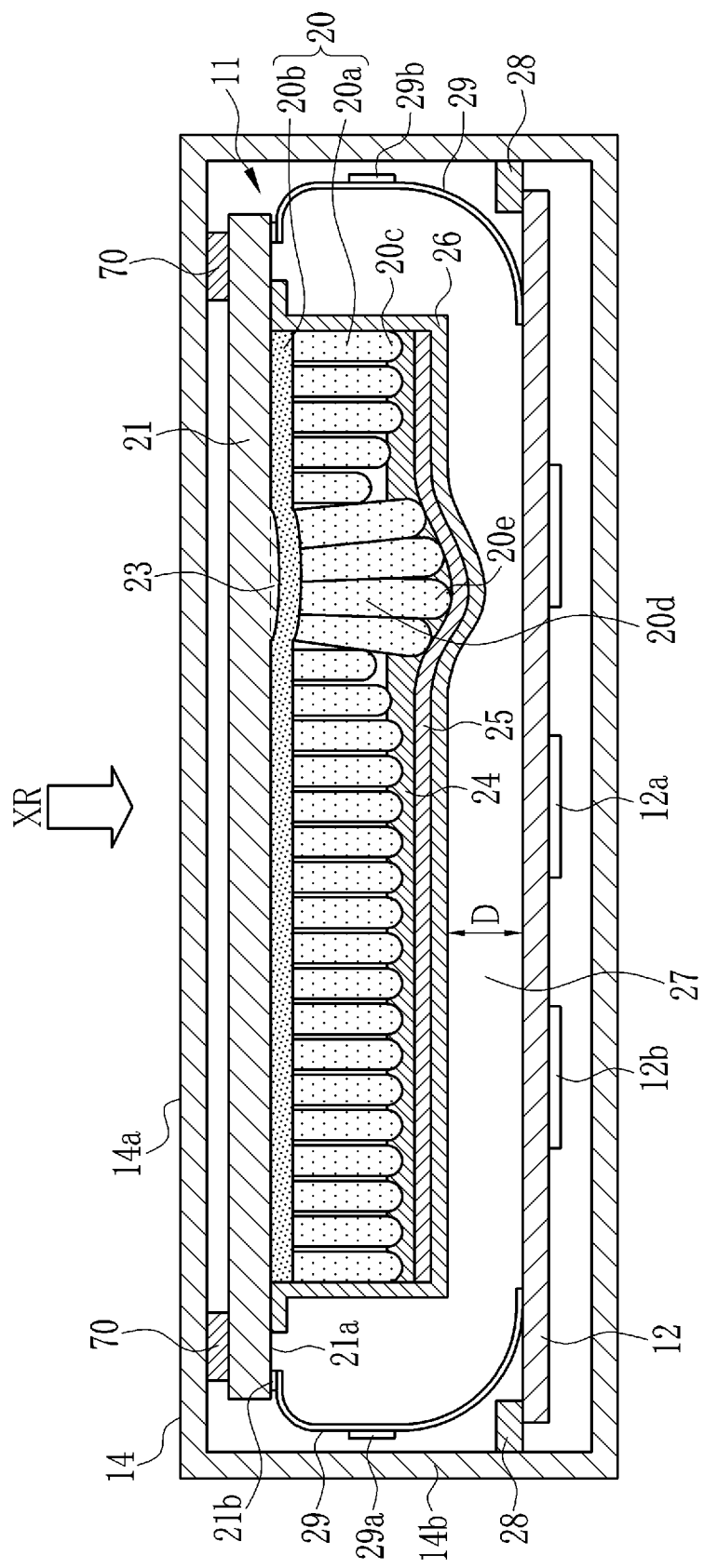
FIG. 6 is a cross-sectional view illustrating a first modified example of the X-ray image detection device.

In the above embodiments, as illustrated in FIG. 2, substantially the entire X-ray incidence side of the photoelectric conversion panel 21 is adhered to the housing 14 through the adhesive layer 22. Note that, as illustrated in FIG. 6, only the outer end portions of the X-ray incidence side of the photoelectric conversion panel 21 may be adhered to the housing 14 through adhesive layers 70. The adhesive layers 70 are provided outside of the scintillator 20. Thereby, the adhesive layer 70 does not absorb the X-rays XR directed to the scintillator 20. As a result, the amount of the X-rays entering the scintillator 20 increases. Instead of the adhesive layer 70, a screw or the like may be used to fix the photoelectric conversion panel 21 to the housing 14.

Figure 7:
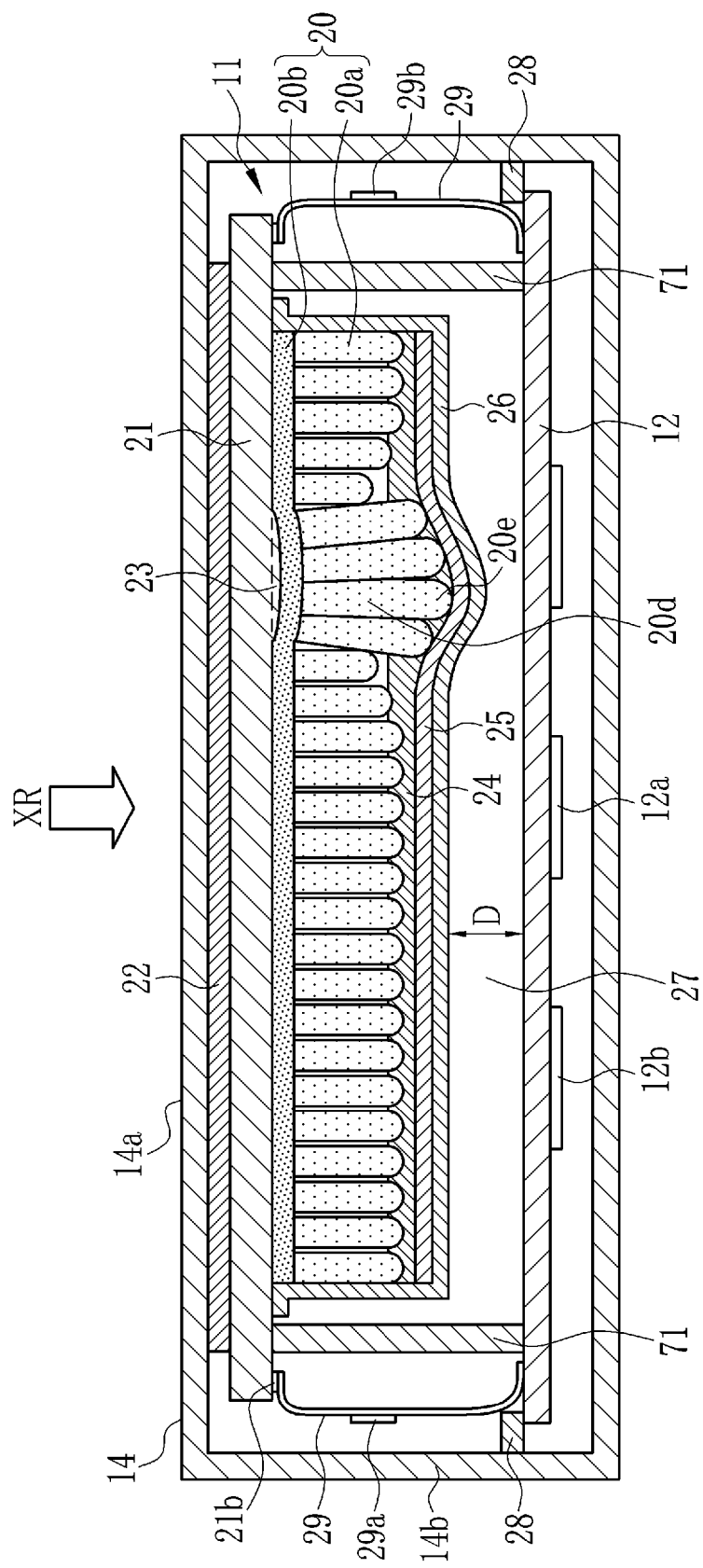
FIG. 7 is a cross-sectional view illustrating a second modified example of the X-ray image detection device.

As illustrated in FIG. 7, a spacer 71 may be provided inside the gap layer 27 between the photoelectric conversion panel 21 and the circuit board 12. The spacer 71 is formed from (or is) an elastic body such as rubber. The spacer 71 is disposed at a peripheral (or outer edge) portion between the photoelectric conversion panel 21 and the circuit board 12 so as to surround the scintillator 20, by way of example. Upper and lower ends of the spacer 71 may be adhered to the photoelectric conversion panel 21 and the circuit board 12, respectively. One of the upper and lower ends may not be adhered. In any case, the spacer 71 prevents the photoelectric conversion panel 21 from bending under a load from the housing 14.

In the case where the upper and lower ends of the spacer 71 are adhered, the scintillator 20 is sealed in a space surrounded by the photoelectric conversion panel 21, the circuit board 12, and the spacer 71. Thereby, the moisture-resistant property of the scintillator 20 is further improved. In this case, the sealing film 26 may be omitted. Furthermore, the adhesive layer 22 may be omitted. The photoelectric conversion panel 21 may be supported only by the circuit board 12 and the spacer 71. In the case where one of the upper and lower ends of the spacer 71 is not adhered, the photoelectric conversion panel 21 is not affected by the occurrence of warpage or curling in the circuit board 12.

Figure 8:
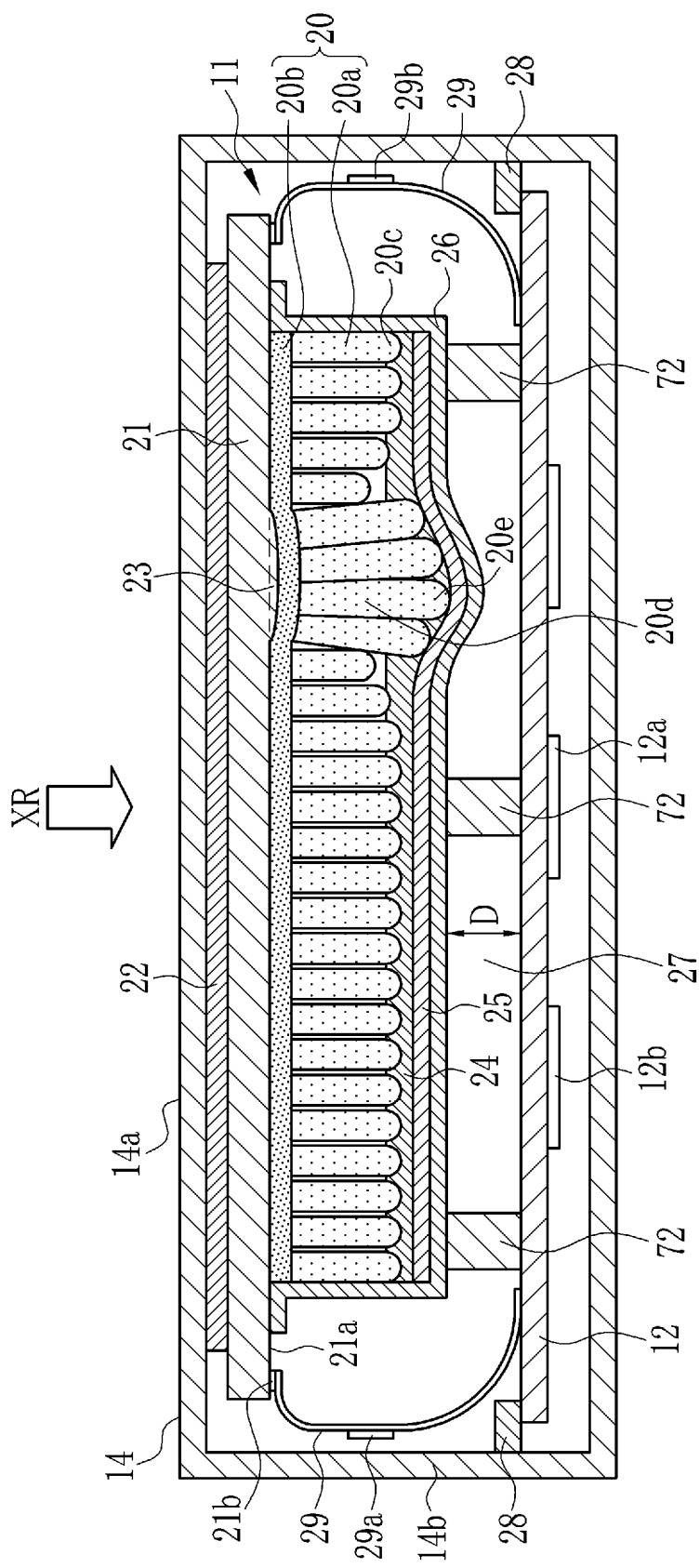
FIG. 8 is a cross-sectional view illustrating a third modified example of the X-ray image detection device.
Figure 9:
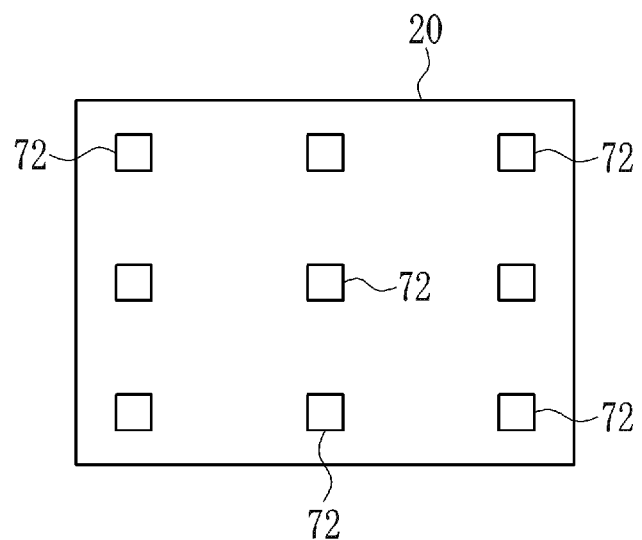
FIG. 9 is a plan view illustrating ribs in a first arrangement.

In the above embodiments, the scintillator 20 is retained by the photoelectric conversion panel 21 through the vapor deposition. The scintillator 20 may fall off or come off from the photoelectric conversion panel 21 due to the self weight of the scintillator 20. To prevent this, ribs 72 may be provided in the gap layer 27 between the scintillator 20 and the circuit board 12 as illustrated in FIG. 8. The rib 72 is formed from (or is) an elastic body such as the rubber. The lower end of the rib 72 is adhered or fixed to the circuit board 12 with an adhesive or the like. The upper end of the rib 72 comes in contact with the sealing film 26 and supports the scintillator 20. The rib 72 has a column-like shape. As illustrated in FIG. 9, the ribs 72 are arranged in a square lattice pattern. In this arrangement, the ribs 72 uniformly support the scintillator 20. The ribs 72 prevent the scintillator 20 from falling off or coming off from the photoelectric conversion panel 21 and also prevent a change in the width (distance) D due to a load on the housing 14 applied by an impact or the like.

Figure 10:
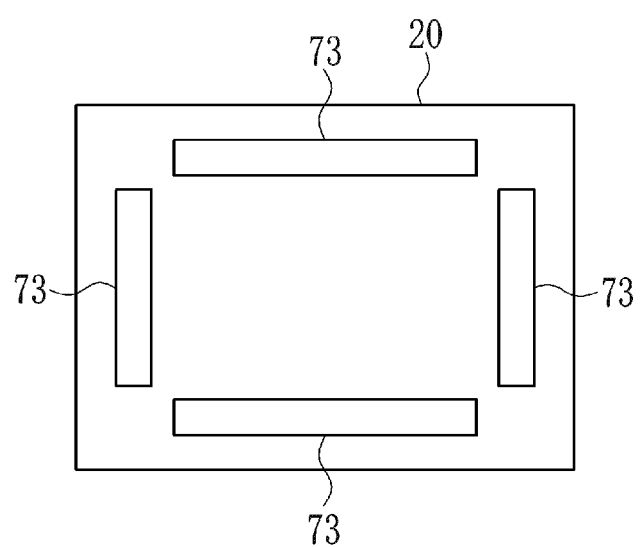
FIG. 10 is a plan view illustrating ribs in a second arrangement.

In the example illustrated in FIG. 9, the rib 72 is also disposed at a center portion of the scintillator 20. In case where the rib 72 comes into contact with the end portion 20e of the abnormally-grown crystal 20d and breaks the adjacent columnar crystals 20a, an image defect occurs at the center portion of the X-ray image. To prevent the image defect, it is preferred to provide ribs 73 at the peripheral (or edge) portions of the scintillator 20 as illustrated in FIG. 10. In this example, the rib 73 has a wall-like shape.

Figure 11:
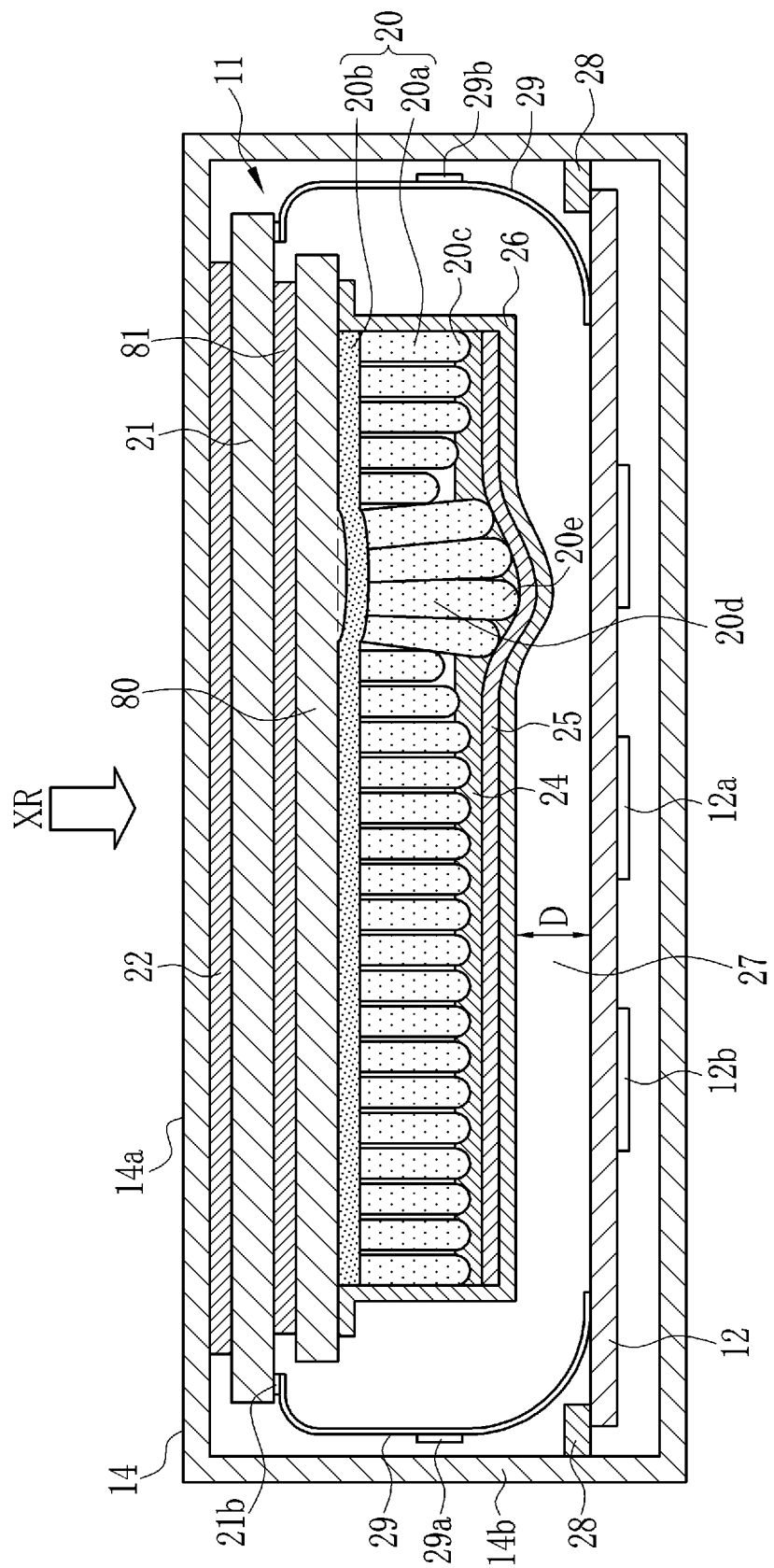
FIG. 11 is a cross-sectional view illustrating a fourth modified example of the X-ray image detection device.

In the above embodiments, the scintillator 20 is directly vapor-deposited on the photoelectric conversion panel 21. Alternatively, as illustrated in FIG. 11, a light-permeable base 80 is adhered or affixed to the opposite side of the radiation incidence side of the photoelectric conversion panel 21. The scintillator 20 is vapor-deposited on the light-permeable base 80. The light-permeable base 80 is adhered to the photoelectric conversion panel 21 through an adhesive layer 81.

The visible light generated in the scintillator 20 passes through the light-permeable base 80 and the adhesive layer 81, and then enters the photoelectric conversion panel 21, so that it is preferred that the light-permeable base 80 and the adhesive layer 81 have high visible-light transmitting properties. Transparent polyimide, polyarylate resin, an OPS (Oriented Polystyrene Sheet) film, aramid, or the like may be used as the material of the light-permeable base 80. Since the light-permeable base 80 is used as the base on which the scintillator 20 is vapor-deposited, it is preferred that the light-permeable base 80 has heat resistance so that it can endure the vapor deposition temperature. The OPS film is most suitable for the light-permeable base 80 (or the material of the light-permeable base 80) because the OPS film has the heat resistance up to approximately 250° C. Light-permeable epoxy resin, acrylic resin, or the like may be used as the material of the adhesive layer 81.

The adhesive layer 81 may have adhesive property which allows the photoelectric conversion panel 21 and the light-permeable base 80, on which the scintillator 20 is vapor-deposited, to be separated from each other easily at the time of repair, for example. The adhesive layer 81 may be omitted. The light-permeable base 80 may be fixed to the housing 14 by pressing the light-permeable base 80 against the photoelectric conversion panel 21.

Figure 12:
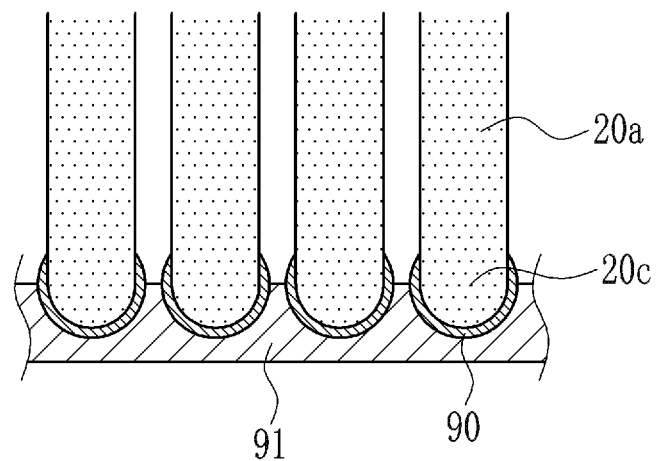
FIG. 12 is a cross-sectional view illustrating a metal thin films formed around end portions of columnar crystals.

In the above embodiments, the light-reflecting film 25 is formed over the protective film 24 of the scintillator 20. The sealing film 26 is formed over the light-reflecting film 25. Alternatively, the sealing film 26 may be formed over the protective film 24. The light-reflecting film 25 may be formed over the sealing film 26. As illustrated in FIG. 12, a metal thin film 90 made from aluminum or the like, which has the light-reflecting property, may be formed by the vapor deposition over the end portion 20c of the columnar crystal 20a. A protective film 91 may be formed from hot-melt resin so as to cover the end portions 20c on which the metal thin films 90 have been formed.

In the above embodiments, the gap layer 27 is filled with the air. Alternatively, the gap layer 27 may be filled with inert gas (e.g. nitrogen, noble gas, or the like). The pressure inside the housing 14 may be reduced to make the gap layer 27 close to vacuum.

In the above embodiments, the circuit board 12 is fixed to the fixing member 28. An insertion rail (not shown) may be provided inside the housing 14. The circuit board 12 is inserted, along the insertion rail, into the housing 14 from the opening (not shown) provided to the side of the housing 14. The circuit board 12 may be fixed to a specific position on the insertion rail. It is preferred to provide a positioning member, inside the housing 14, in a position opposing the opening and fix the circuit board 12 after the circuit board 12 is positioned with the positioning member. The photoelectric conversion panel 21 and the scintillator 20 may be inserted into the housing 14 and fixed in like manner.

In the above embodiments, the active layer 32a of the TFT 32 is formed from the amorphous silicon. Alternatively, the active layer 32a may be formed from amorphous oxide (for example, In—O type), organic semiconductor material, carbon nanotube, or the like.

In the above embodiments, the semiconductor layer 33b of the PD 33 is formed from the amorphous silicon. Instead, the semiconductor layer 33b may be formed from organic photoelectric conversion material (e.g. quinacridone-based organic compound or phthalocyanine-based organic compound). The amorphous silicon has a wide absorption spectrum. The organic photoelectric conversion material, on the other hand, has a sharp absorption spectrum in the visible range, so that it absorbs the visible light generated by the scintillator 20 but hardly absorbs electromagnetic waves other than the visible light. As a result, noise is prevented or reduced.

Note that the above-described modifications may be used in combination as necessary. In the above embodiments, the X-rays are used as the radiation. The radiation other than the X-rays, for example gamma rays, alpha rays, or the like may be used. The present invention is described with the above-described embodiments using the electronic cassette, being the portable radiographic image detection device, by way of example. The present invention is also applicable to a radiographic image detection device of a standing type or lying type, a mammography device, and the like.

Various changes and modifications are possible in the present invention and may be understood to be within the present invention.

What is claimed is:

1. A radiographic image detection device comprising:
a scintillator containing cesium iodide and converting radiation into visible light, the scintillator having a non-columnar crystal layer and a plurality of columnar crystals formed on the non-columnar crystal layer;
a photoelectric conversion panel on which the scintillator is vapor-deposited and in which a plurality of pixels for photoelectrically converting the visible light into charges are formed, the non-columnar crystal layer being in close contact with the photoelectric conversion panel;
a circuit board provided with a signal processor for generating image data based on the charges generated by the photoelectric conversion panel;
a gap layer for preventing the plurality of columnar crystals from contacting to the circuit board, the gap layer being provided between the scintillator and the circuit board, the gap layer being provided with a first support, one of ends of the first support being fixed to the circuit board and the other end supporting the scintillator, wherein the gap layer being filled with air or inert gas; and
a housing for accommodating the photoelectric conversion panel, the scintillator, the gap layer, and the circuit board in this order from a radiation incidence side on which the radiation is incident from a radiation source at the time of imaging.

2. The radiographic image detection device according to claim 1, wherein the first support supports a peripheral portion of the scintillator.

3. The radiographic image detection device according to claim 2, wherein the first support is an elastic body.

4. The radiographic image detection device according to claim 1, further comprising a second support for supporting between the photoelectric conversion panel and the circuit board.

5. The radiographic image detection device according to claim 4, wherein the second support surrounds the scintillator.

6. The radiographic image detection device according to claim 1, wherein the housing has a monocoque structure.

7. The radiographic image detection device according to claim 1, wherein the photoelectric conversion panel and the circuit board are individually fixed to the housing.

8. The radiographic image detection device according to claim 1, further comprising a sealing film that surrounds the scintillator.

9. The radiographic image detection device according to claim 8, further comprising a light-reflecting film that reflects the visible light released from end portions of the columnar crystals.

10. The radiographic image detection device according to claim 9, further comprising a protective film that covers the end portions of the columnar crystals, and the light-reflecting film is formed over the protective film, and the sealing film covers the light-reflecting film.

11. The radiographic image detection device according to claim 10, wherein the pixel has a photodiode for converting the visible light into the charge and a switching element for reading out the charge generated by the photodiode.

* * * * *